US008827041B2

(12) United States Patent
Brown et al.

(10) Patent No.: US 8,827,041 B2
(45) Date of Patent: Sep. 9, 2014

(54) CARRIER CAR DOOR ASSEMBLY

(76) Inventors: Michael E. Brown, Kings Mill, OH (US); Christopher L. Michael, Maineville, OH (US)

( * ) Notice: Subject to any disclaimer, the term of this patent is extended or adjusted under 35 U.S.C. 154(b) by 835 days.

(21) Appl. No.: 12/535,965

(22) Filed: Aug. 5, 2009

(65) Prior Publication Data

US 2011/0030166 A1 Feb. 10, 2011

(51) Int. Cl.

| | |
|---|---|
| ***A61F 13/15*** | (2006.01) |
| ***E04H 3/00*** | (2006.01) |
| ***E05F 1/10*** | (2006.01) |
| ***E05F 15/04*** | (2006.01) |
| ***E05F 15/12*** | (2006.01) |
| *E05G 7/00* | (2006.01) |

(52) U.S. Cl.

CPC ............ *E05F 15/127* (2013.01); *E05F 1/1066* (2013.01); *E05F 15/04* (2013.01); *E05G 7/00* (2013.01)

USPC .................. 186/52; 186/50; 186/51; 186/58; 186/22; 49/339; 49/340; 49/345; 187/336; 187/337; 187/342

(58) Field of Classification Search

USPC .................. 186/41, 37, 49–53, 55, 58, 60, 7, 186/14–17, 21, 22, 26; 902/33; 49/339–341, 345; 187/336–342, 315; 104/127–129

See application file for complete search history.

(56) References Cited

U.S. PATENT DOCUMENTS

| | | | | |
|---|---|---|---|---|
| 2,613,762 A * | 10/1952 | McClintock | .................... | 186/37 |
| 3,881,573 A * | 5/1975 | Cotter et al. | .................... | 186/37 |
| 4,605,102 A * | 8/1986 | Morano et al. | .................. | 186/37 |
| 5,054,605 A * | 10/1991 | Bavis | ......................... | 198/750.1 |
| 5,172,791 A * | 12/1992 | Couvrette | ....................... | 186/37 |
| 5,361,891 A * | 11/1994 | Greene et al. | ................. | 198/797 |
| 5,562,383 A * | 10/1996 | Iwai et al. | .................. | 414/217.1 |
| 6,196,377 B1 * | 3/2001 | Brown | .......................... | 198/839 |
| 7,500,551 B1 * | 3/2009 | Greene | ...................... | 198/475.1 |
| 2002/0104713 A1 * | 8/2002 | Brown et al. | .................. | 186/41 |

* cited by examiner

*Primary Examiner* — Jeffrey Shapiro
(74) *Attorney, Agent, or Firm* — Dinsmore & Shohl LLP

(57) ABSTRACT

Carrier car door assemblies respectively comprising a carrier car comprising a body, a door, a drive mechanism, a driven mechanism, and a magnetic release mechanism are disclosed herein. The carrier car travels along a track system between teller and customer stations to transport materials there-between. The door is connected to the body and movable between a door-closed position and a door-open position. The drive mechanism is connected to the body and to the driven mechanism so that the drive and driven mechanisms synchronously move between respective door-closed positions and door-open positions. The magnetic release mechanism is connected to the driven mechanism and moves from a magnetically coupled state to a magnetically de-coupled state when a user manually moves the door from the door-open position to the door-closed position. The magnetic release mechanism in the magnetically coupled state synchronously moves with the driven mechanism between door-closed and door-open positions.

19 Claims, 12 Drawing Sheets

CARRIER CAR DOOR ASSEMBLY

BACKGROUND

Many pharmacies offer drive-thru services for their customers through which customers may drop-off and pick-up prescriptions, medications, and therapeutic products. Conventional carrier car door assemblies typically utilize cars for conveying materials between a customer station and a teller station. The cars generally are for traveling between the two stations via track systems, such as pneumatic tube systems or mechanical track systems.

SUMMARY OF THE INVENTION

Embodiments of the present invention generally relate to a carrier car door assembly. More particularly, embodiments relate to carrier cars and track systems suitable for use with carrier car door assemblies. The carrier car door assembly serves the function of transporting materials, such as medicines and therapeutic products, between a customer station outside of a facility and a teller station inside of a facility. Generally, a linkage system integrated with the carrier car controls the moving of the carrier car's doors between a door-closed position and a door-open position. Upon arrival at a station, the carrier car engages a stabilizer positioned at an end of the track system that activates the automatic opening of the doors via the linkage system. This linkage system comprises a magnetic release mechanism that assists in not only the automatic opening and closing of the doors, but also allows the doors to be opened and closed manually by a user of the carrier car. Manually closing the doors while the carrier car is engaged with the stabilizer de-couples magnets of a rotary arm from magnets of rotary plates that make up the magnetic release mechanism, thereby allowing the doors to close independently of a de-coupled magnetic release mechanism. As the carrier car departs from the station and the drive mechanism disengages the stabilizer, doors that have not been manually closed close automatically via the linkage system. Whereas, doors that have been closed manually will stay closed and the de-coupled magnetic release mechanism automatically re-couples upon the carrier car departing the stabilizer, thereby preparing the doors to open again automatically upon reaching the stabilizer positioned at the opposite station.

BRIEF DESCRIPTION OF THE DRAWINGS

The following detailed description of the various embodiments of the present invention can be best understood when read in conjunction with the following drawings, where like structure is indicated with like reference numerals and in which.

Figure 1:
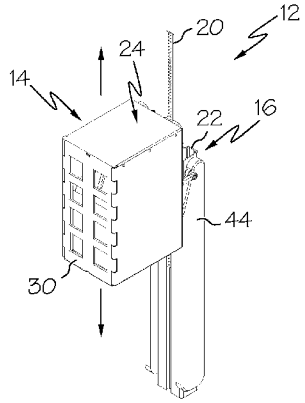
FIG. 1 is an illustration of a perspective view of a carrier car door assembly according to one embodiment of the present invention.
Figure 2:
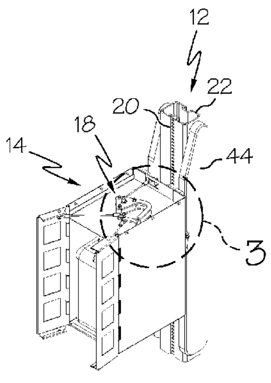
FIG. 2 is an illustration of a perspective view of a carrier car door assembly comprising a carrier car and a driven mechanism rotated such that the doors to the carrier car are in the door-open position according to the embodiment illustrated in FIG. 1.

The embodiments set forth in the drawings are illustrative in nature and are not intended to be limiting of the invention defined by the claims. Moreover, individual aspects of the drawings and the invention will be more fully apparent and understood in view of the detailed description.

DETAILED DESCRIPTION

FIGS. 1, 2, 4, and 11 illustrate an exemplary embodiment of a carrier car door assembly 12. The carrier car door assembly 12 generally comprises a carrier car 14, a track system 16, and a linkage system 18. The carrier car door assembly 12 is operable to transport the carrier car 14, and any materials held therein, so that it travels along the track system 16 between a customer station outside of a facility and a teller station inside of a facility. For example, in one embodiment, the facility is a pharmacy where pharmacy representatives at the teller station and customers at the customer station exchange materials, such as, but not limited to, prescription slips, cash, credit cards, insurance cards, medications, and therapeutic products, through the carrier car door assembly 12 of the pharmacy. It is contemplated, however, that embodiments of the carrier car door assembly 12 of the present invention may be employed at any variety of facilities where materials are exchanged between interconnected customer stations outside of facilities and teller stations inside of facilities, between interconnected stations inside of facilities, or between interconnected stations outside of facilities.

The customer stations and the teller stations, as described herein, are interconnected by the track system 16 of the carrier car door assembly 12. The track system 16 may be pneumatically-powered or mechanically-driven. For example, in the embodiments illustrated in FIGS. 1, 2, 4, and 11, the track system 16 is mechanically-driven and comprises a rotating, continuous track 20 and a track support 22. The continuous track 20 may be, but is not limited to, a chain, tape, belt, or other transport-enabling device suitable for performing the functions of the continuous track 20 described herein or otherwise known to one of ordinary skill in the art. The track support 22 generally is configured as a bracket or other supportive device that supports the continuous track 20, and a carrier car 14 transported thereon, between the customer station and the teller station.

Figure 6A:
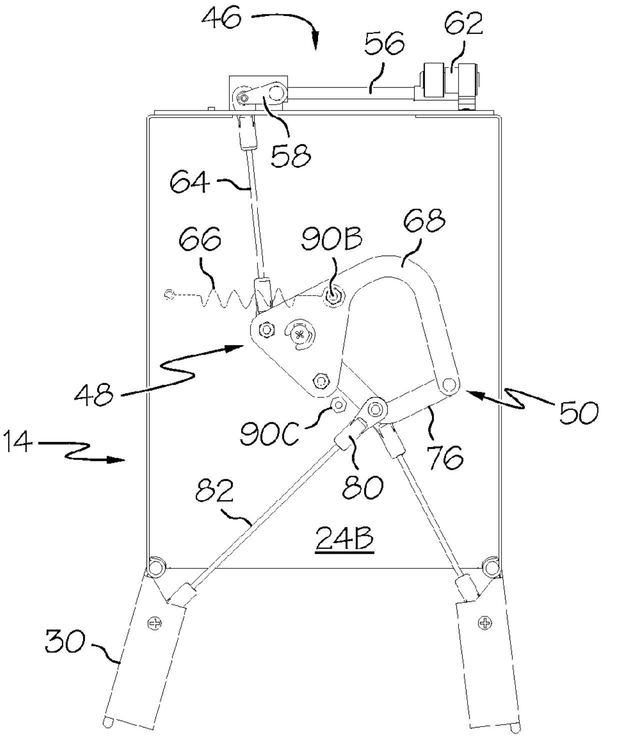
FIGS. 6A and 6B are illustrations of views of a carrier car and a linkage system when doors of the carrier car are in the door-open position according to another embodiment of the present invention.
Figure 6B:
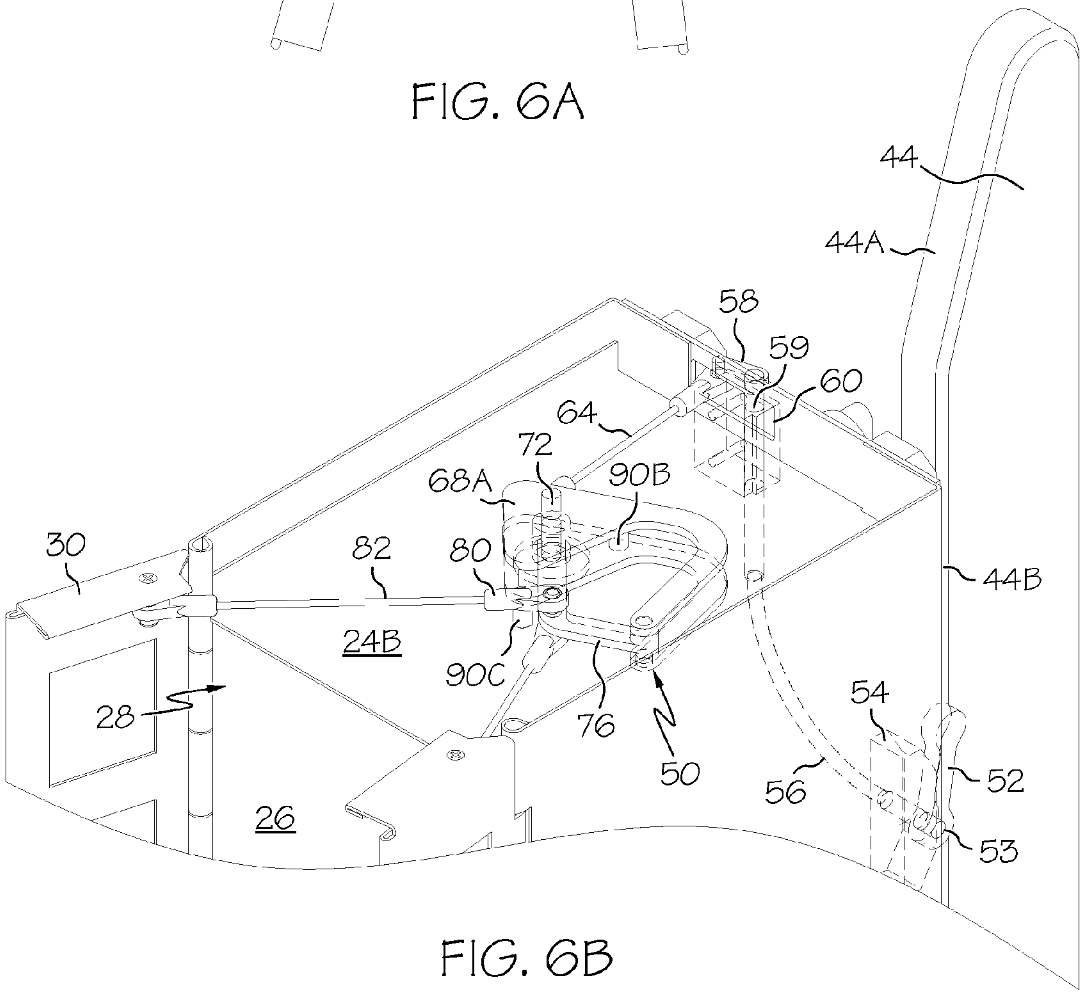
Figure 7A:
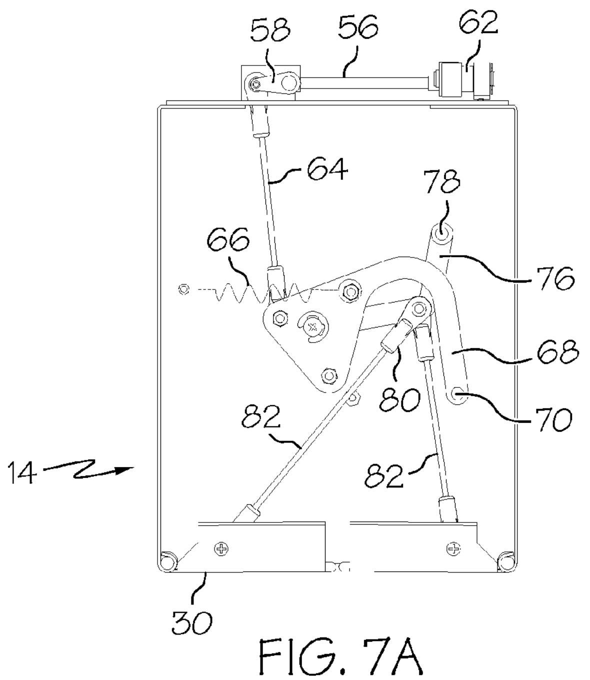
FIGS. 7A and 7B are illustrations of views of a carrier car and a linkage system when a magnetic release mechanism is released to a magnetically de-coupled state due to a manual closing of doors of the carrier car according to another embodiment of the present invention.
Figure 7B:
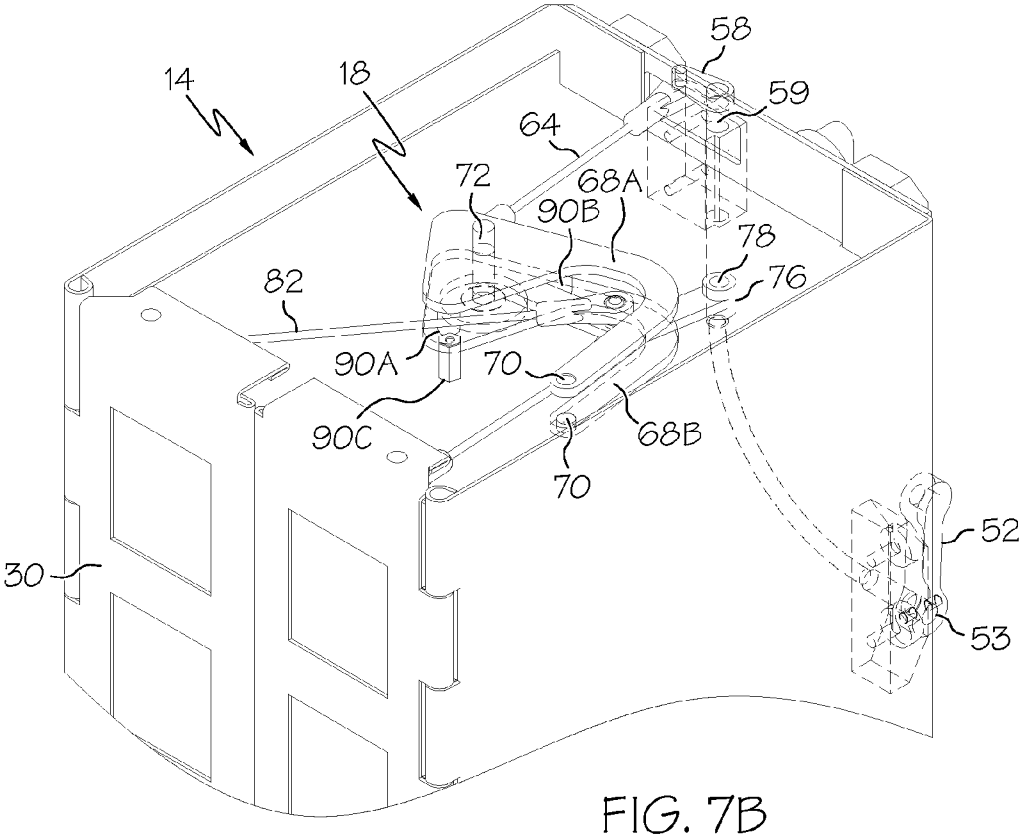

In addition, the track system 16 generally comprises at least one stabilizer 44 positioned at or proximal to each station. Referring to FIG. 6B, the stabilizers 44 generally are configured as brackets having a ramped portion 44A and a level portion 44B (e.g., substantially vertical). The stabilizers 44 may coordinate with the drive mechanism 46 to actuate the driven mechanism 48 to automatically open and close the doors 30 of the carrier car 14. It is contemplated that the continuous track 20, the track support 22, and the stabilizer 44 may be configured from one or more of any variety of materials, such as, but not limited to, metals, plastics, polymers, composites, and combinations thereof, and manufactured in one or more of any variety of manners so long as the continuous track 22, the track support 22, and the stabilizers 44 adequately perform the functions described herein or otherwise known to one of ordinary skill in the art.

Embodiments of the carrier car 14 of the carrier car door assembly 12 are shown in FIGS. 1, 2, 4-8, 10, and 11. The carrier car 14, and components thereof, may be manufactured through one or more of any variety of methods and may be configured of one or more of any variety of materials so long as the carrier car 14 may adequately perform the functions described herein or otherwise known to one of ordinary skill in the art. Such materials may include, but are not limited to, metals, plastics, polymers, composites, and combinations thereof. It further is contemplated that the carrier car 14 may be manufactured using common sheet metal fabrication, machining, and/or injection molding processes, or may be purchased parts from vendors. The components are joined in a simple assembly using methods conventional to the trade of carrier car design and manufacturing. Also, in one exemplary embodiment, the carrier car 14 may be designed such that it is not heavier or costlier to manufacture and/or maintain than conventional cars. In one exemplary embodiment, the carrier car 14 may be manufactured as follows: fold carrier car body up from wrap around part; single layer opposite the end with a door actuation mechanism; the folds assume a deeper than wide "U" channel; one or more series of holes are provided so the parts can be hand folded so as to concentrate the stress and cause the folds to be in the correct locations. It is also contemplated that a three ton press may be tooled to make the folds under power, rather than through hand folding. In addition, the carrier car 14 may be retrofitted for application to existing, deployed carrier car door assemblies and track systems.

Figure 8A:
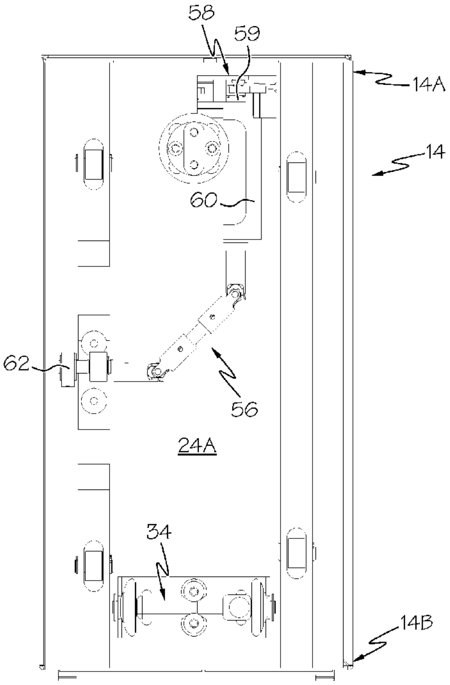
FIGS. 8A and 8B are illustrations of perspective views of a carrier car and a linkage system according to another embodiment of the present invention.
Figure 8B:
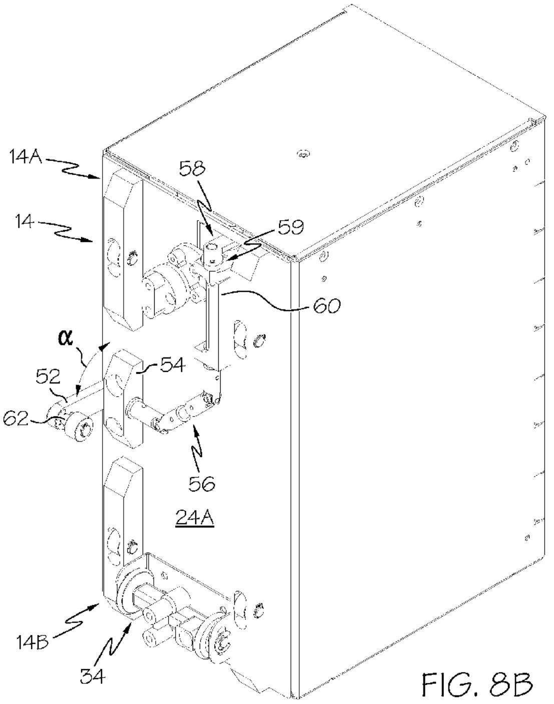

The carrier car 14 generally comprises a body comprising a plurality of side walls. The side walls may include a plurality of exterior walls 24, a plurality of interior walls 26, an interior chamber 28, one or more doors 30, and one or more hinges 32. The exterior back wall 24A of the carrier car 14 is secured to the continuous track 20 such that the carrier car 14 may move over the track support 22 between the customer station and the teller station with rotation of the continuous track 20. More particularly, as shown in FIGS. 8A and 8B, the carrier car 14 may further comprise a wheel assembly 34 secured to the exterior back wall 24A that couples to the continuous track 20 and guides the carrier car 14 along the track support 22. In addition, the interior walls 26 are configured so as to create the interior chamber 28 of the carrier car 14 in which the materials to be transported between the teller and customer stations may be placed. A package bail 36 or other container, whether open-ended or with a closable lid, may be positioned in the interior chamber 28 to secure the transaction to occur between the stations. The package bail 36 may be affixed in the interior chamber 28 or may be removable from the interior chamber 28 and the carrier car 14 for easier insertion and removal of materials. In addition, liners may be applied to the top, bottom, back, and/or side interior walls 26 of the carrier car 14. These liners may provide a cushioning layer to the interior chamber 28 of the carrier car 14, may seal any gaps between adjacent interior walls 26 of the carrier car to preclude the falling of materials therethrough, and/or may perform an ascetic purpose. Further, one or more areas of the exterior walls 24 and/or the interior walls 26 may be preserved for the application of labels. These labels may present instructions for use of the carrier car door assembly 12, present promotional information, provide decorative appeal, and/or other information or images. Also, the walls 24, 26 of the carrier car 14 may be finished with one or more of any variety of finishes or applications, such as, but not limited to, a powder coat or a polymer coat, so as to protect the carrier car 14 from environmental elements and/or to provide decorative appeal.

Figure 10:
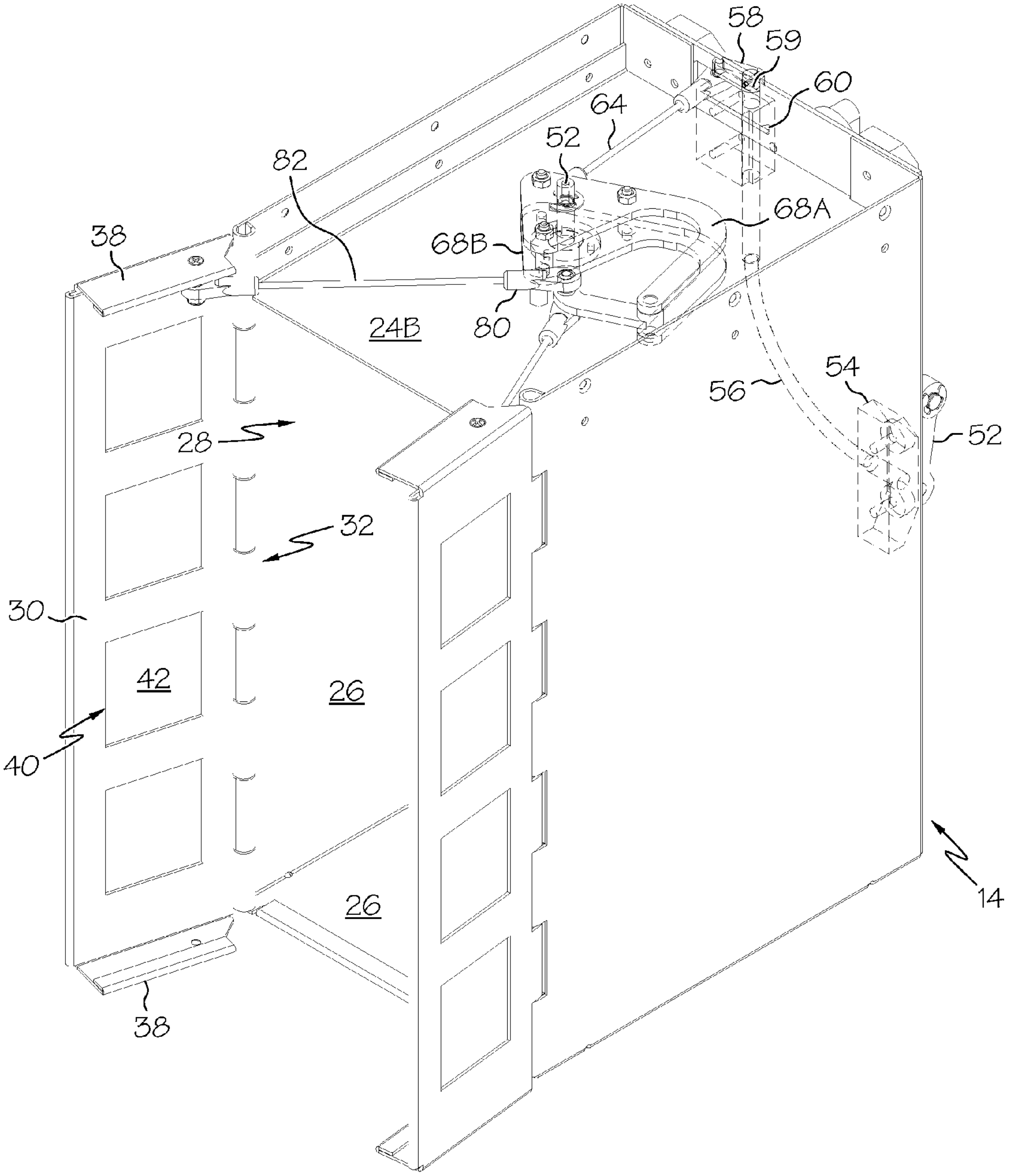
FIG. 10 is an illustration of a perspective view of a carrier car and a linkage system according to another embodiment of the present invention.

As mentioned above, the carrier car 14 also comprises one or more doors 30 connected to the body. These doors 30 are movable about one or more hinges 32 with the walls 24, 26 of the carrier car 14 so as to move between a door-closed position and a door-open position and, thereby, open and close the interior chamber 28 of the carrier car 14. The opening and closing of the doors 30 described herein thus refer to the moving of the doors 30 to door-open position and the door-closed position, respectively. While the hinges 32 are shown in FIG. 10 to be configured as curled hinges, it is contemplated that other or additional hinges may be used as well. The presence of the doors 30 and the ability to open and close the interior chamber 28 secures the materials placed therein during transportation between the two stations. To further secure the materials placed in the interior chamber 28 and prevent those materials, such as credit cards and cash, from sliding out from under closed or partially closed (when opening, closing, or obstructed) doors 30, the doors 30 may have scalloped edges 38, as shown in FIG. 10. Alternatively, or in addition thereto, the doors 30 may have sealing flaps, rubber bulb edgings, or other escape prohibitive devices applied to edges of the doors 30. In addition, a spring clip or other securing device may be provided in the interior chamber 28 or in the package bail 36 to secure materials from falling out of the carrier car 14. Further, the doors 30 may comprise one or more windows 40 for viewing of the materials contained in the interior chamber 28. These windows 40 may be closed or covered with a clear acrylic material or other relatively transparent material 42. In one exemplary embodiment, the doors 30 are configured as a 0.050 inch aluminum sheet folded over an acrylic lens positioned in a window 40 of the aluminum sheet.

The linkage system 18 of the carrier car door assembly 12 controls the automatic opening and closing of the doors 30 with the arrival and departure of the carrier car 14 at either of the teller and customer stations. The linkage system 18 also permits the manual opening and closing of the doors 30 without interfering with subsequent automatic opening and closing of the doors 30. The linkage system 18 generally comprises a drive mechanism 46 and a driven mechanism 48. The magnetic release mechanism 50 described in greater detail herein also may be incorporated into or described as a component of the linkage system 18. In addition, the carrier car door assembly 12 may comprise a spring 66, which may be referred to herein as integrated into or described as a component of the linkage system 18. All of these components interact to control the automatic opening and closing of the doors 30 and/or permit the manual opening and closing of the doors 30. More particularly, and as is described in greater detail below, as the drive mechanism 46 moves from a door-closed position to a door-open position, it moves the driven mechanism 48 from a door-closed position to a door-open position. Various embodiments of the linkage system 18 are shown in FIG. 9.

The drive mechanism 46 is connected to the body of the carrier car 14 and generally comprises a middle rotary arm 52 rotatable about a rotatable joint 53 positioned adjacent to an exterior back wall 24A of the carrier car 14, a middle support block 54 that fixedly couples the rotatable joint 53 of the middle rotary arm 52 to the exterior back wall 24A, an end rotary arm 58 rotatable about a rotatable joint 59, an end support block 60 that fixedly couples the rotatable joint 59 of the end rotary arm 58 to the exterior back wall 24A, an angular joint 56 that couples the middle and end rotary arms 52, 58 and is actuatable in a substantially linear direction due to the rotation of the middle and end rotary arms 52, 58, and an extension rod 64 that couples the end rotary arm 58 to the driven mechanism 48 and is pivotable with respect to an exterior top wall 24B of the carrier car 14.

Figure 3:
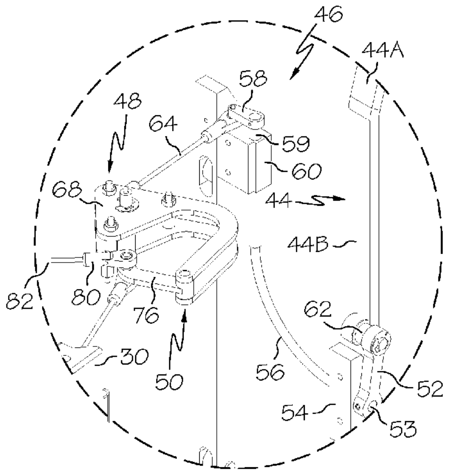
FIG. 3 is an illustration of an enlarged view of a linkage system comprising a drive mechanism and a driven mechanism according to another embodiment of the present invention.
Figure 4A:
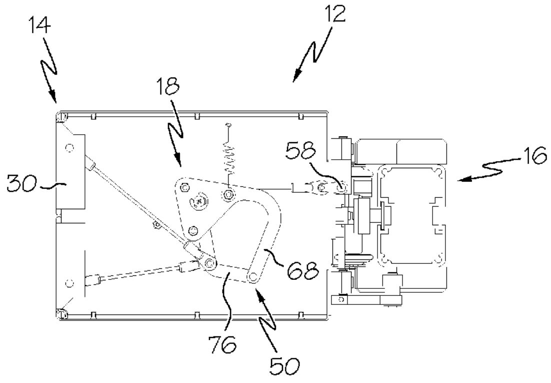
FIGS. 4A-4F are illustrations of a series of steps for the moving of the doors between a door-closed position and a door-open position where the closing of the doors is done manually such that a user of the carrier car door assembly de-couples a magnetic release mechanism according to another embodiment of the present invention.
Figure 4B:
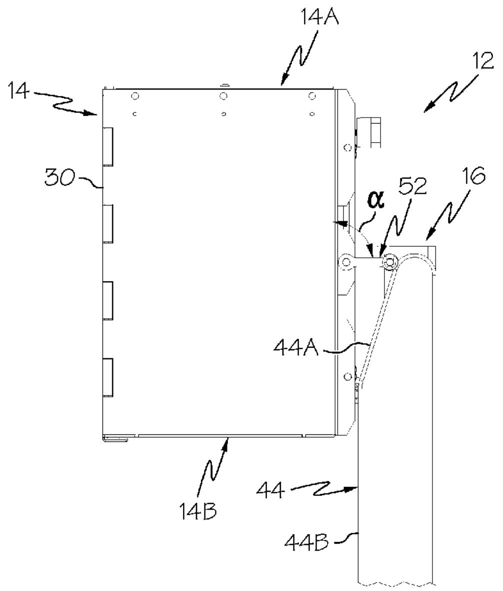
Figure 4C:
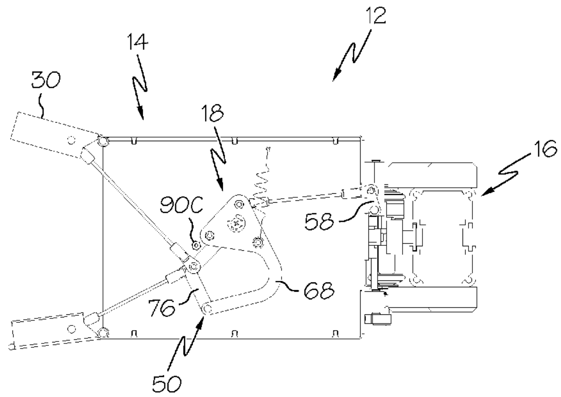
Figure 4D:
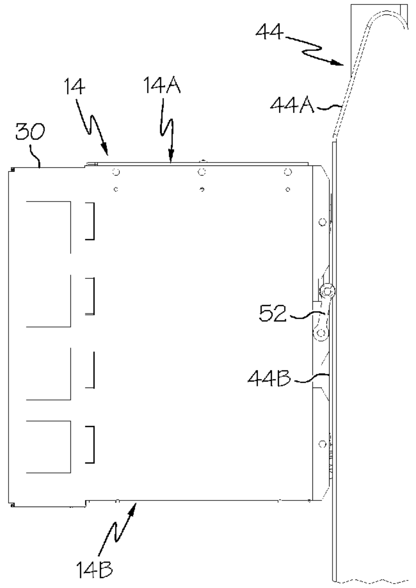
Figure 4E:
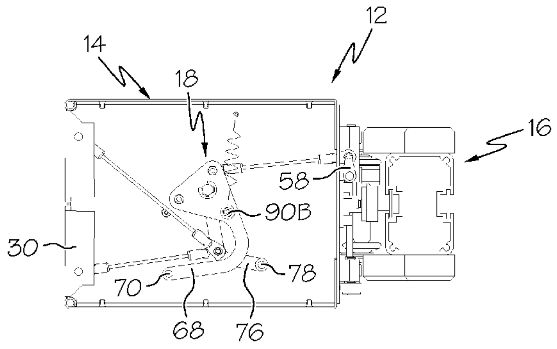
Figure 4F:
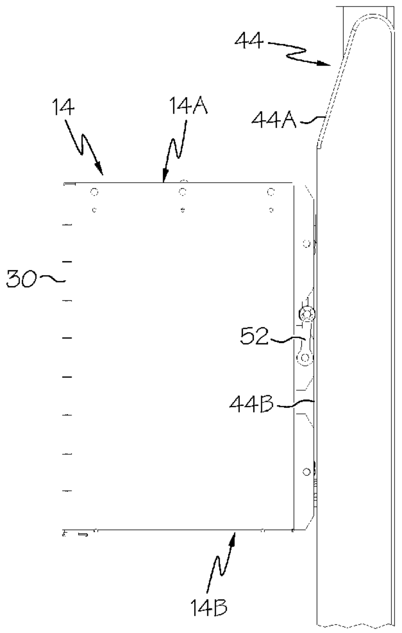
Figure 5A:
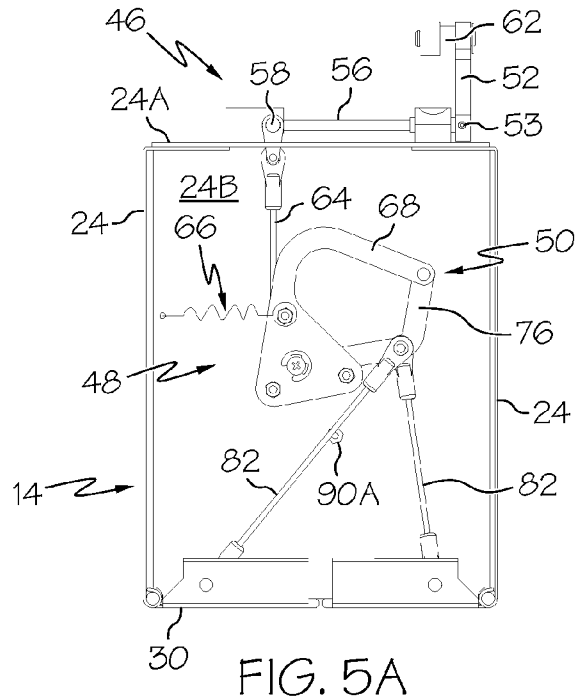
FIGS. 5A and 5B are illustrations of views of a carrier car and a linkage system when doors of the carrier car are in the door-closed position according to another embodiment of the present invention.
Figure 5B:
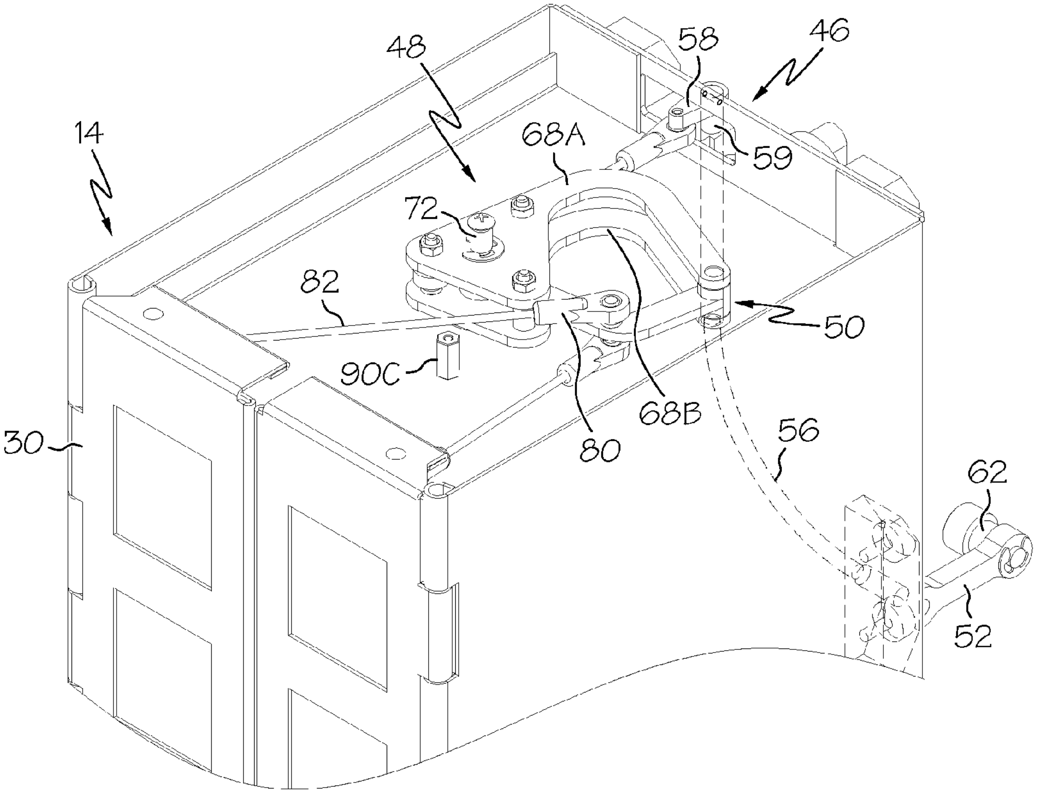

As shown in FIGS. 3, 5, and 8, the middle rotary arm 52 comprises a wheel 62 positioned at an end of rotary arm 52 that is distal from the rotatable joint 53. The rotatable joint 53 is fixedly coupled to the middle support block 54. The wheel 62 is configured to engage and roll along the ramped and level portions 44A, 44B of the stabilizers 44 when the carrier car 14 arrives at and/or departs from the stations. More particularly, as the carrier car 14 is transported along the track system 16 between stations, the middle rotary arm 52 projects at an angle α relative to the exterior back wall 24A (i.e., substantially vertical wall) of the carrier car 14 as shown in FIG. 3. The rotatable joint 53 enables the middle rotary arm 52 to rotate and/or pivot about the joint 53 (the middle rotary arm's connection with the middle support block 54) such that the middle rotary arm 52 projects at an angle α from about 0 degrees to about 90 degrees relative to the exterior back wall 24A. This angular projection of the middle rotary arm 52, and the wheel 62 provided at the distal end thereof, enables the wheel 62 to engage and roll along the stabilizer 44 as described above. It is contemplated that a roller, ball, pad, or other device capable of adequately performing the functions of the wheel 62 as described herein may be provided to the distal end of the middle rotary arm 52 as an alternative to the wheel 62. In one exemplary embodiment, a brass wheel is positioned at the distal end of the middle rotary arm 52 and directly engages the stabilizer 44. The brass wheel is supported by a stainless steel axle fastened with retaining rings to the distal end of the middle rotary arm 52. As such, the middle rotary arm 52 may roll along the ramped and level portions 44A, 44B, respectively, of the stabilizers 44.

Further, as shown in FIGS. 8A and 8B, a middle rotary arm 52 may be applied centrally, or substantially centrally, to the exterior back wall 24A as long as the middle rotary arm 52 engages and advances along the stabilizer 44 and as long as there is sufficient clearance space between the exterior back wall 24A of the carrier car 14 and the continuous track 20, track support 22, and the stabilizer 44 to permit adequate vertical rotational movement (e.g., about a horizontal axis of joint 53) of the middle rotary arm 52 as it advances along the stabilizer 44. The clearance space generally is about 1/16 inch. Due to the limited clearance space, conditions of the track system 16 may be monitored for over-crimping or severe wearing or other conditions that may hinder, obstruct, or otherwise interfere with rotation of the middle rotary arm 52 over the stabilizer 44 and/or the transport of the carrier car 14 along the track system 16. In alternative embodiments, one or more middle rotary arms 52 may be applied to either end or both ends (i.e., top 14A and bottom 14B) of the exterior back wall 24A of the carrier car 14 such that at least one middle rotary arm 52 is positioned to engage a stabilizer 44 since the carrier car door assembly 12 may be configured such that only one end of the carrier car 14 advances along the stabilizer 44 while the other end of the carrier car 14 remains positioned directly adjacent to the continuous track 20 and track support 22, rather than along the stabilizer 44. Further, it is contemplated that the angle of approach of the carrier car 14 and the wheel 62 to the stabilizer 44 generally is not too low so as cause the carrier car 44 to get stuck on the stabilizer 44. In addition, the surface area of the wheel 62 to engage the stabilizer 44 generally is sufficient to prevent substantial wearing of the stabilizer 44.

The angular joint 56, shown in greatest detail in FIG. 8, traverses a length over the exterior back wall 24A and couples the middle rotary arm 52 and the end rotary arm 58. The angular joint 56 actuates with rotational movements of the middle and/or end rotary arms 52, 58, respectively, so that the angular joint 56 translates rotational movement of one of the middle and end rotary arms 52, 58, respectively, to the other of the middle and end rotary arms 52, 58 such that the end rotary arm 58 and the angular joint 56 synchronously move with rotation of the middle rotary arm 52. Thereby, the angular joint 56 translates upward vertical rotational movement of the middle rotary arm 52 into clockwise horizontal rotational movement of the end rotary arm 58 such that the two rotary arms 52, 58 rotate simultaneously in a door-opening process, as described herein. In addition, the angular joint 56 translates counterclockwise horizontal rotational movement of the end rotary arm 58 into downward vertical rotational movement of the middle rotary arm 52 such that the two rotary arms 52, 58 rotate simultaneously in a door-closing process, as described herein.

As shown in FIGS. 3, 4A, 4B, 4E, 5-8, and 10, the end rotary arm 58 generally, but not necessarily, comprises a pear-like shape where the base of end rotary arm 58 is rotatably connected to the rotatable joint 59, which is fixedly coupled to the end rotary block 60, while the apex of the end rotary arm 58 is pivotably connected to the extension rod 64 via a ball joint 80 or other pivotable connector. The extension rod 64 connects the end rotary arm 58 to the driven mechanism 48 such that rotational movements of the middle and end rotary arms 52, 58, respectively, are translated to the driven mechanism 48 by the extension rod 64. The end rotary arm 58 generally is positioned near a top 14A of the carrier car 14 such that the extension rod 64 may extend over the exterior top wall 24B of the carrier car 14 to the driven mechanism 48 rotatably secured to the exterior top wall 24B. More particularly, as shown in FIG. 9, the extension rod 64 of the drive mechanism 46 is rotatably coupled to the rotary plates 68 via a ball joint 80 and a bolt 84 and nut 86, or other one or more rotatably connective devices. The extension rod 64 may have one of any variety of cross-sectional shapes and/or may be threaded and unthreaded.

In the exemplary embodiment, the driven mechanism 48, at least partially shown in FIGS. 2, 3, 4A, 4B, 4E, 5-7, and 9-11, cooperates with and is movably connected to the drive mechanism 46 to control the automatic opening and closing of the doors 30 of the carrier car 14. In addition, the driven mechanism 48 may comprise the magnetic release mechanism 50 movably connected thereto, which permits the manual opening and closing of the doors 30. The driven mechanism 48 may further comprise a pivot bar 72 secured to the exterior top wall 24B of the carrier car 14, two rotary plates 68 (i.e., upper 68A and lower 68B) rotatably connected about the pivot bar 72, two rotary plate magnets 70 disposed at an end of the respective rotary plates 68A and 68B distal from the pivot bar 72, a rotary arm 76 positioned between the upper rotary plate 68A and the lower rotary plate 68B and rotatably connected about the pivot bar 72, and a rotary arm magnet 78 positioned at an end of the rotary arm 76 distal from the pivot bar 72. The driven mechanism 48 may also further comprise a pivot bar plate 74, a plurality of ball joints 80, at least two rods 82, a plurality of bolts 84, a plurality of nuts 86 corresponding with the bolts 84, and a plurality of one or more variously configured bearings 88, such as ball bearings, which may assist in securing the different components of the driven mechanism together in this one exemplary embodiment and may facilitate lateral rotation of various components of the driven mechanism 48 as described herein.

As shown in FIGS. 4A, 4B, 4E, 5A, 6A, and 7A, the carrier car door assembly 12 may further comprise a spring 66. The spring 66 generally is coupled at one end to the exterior top wall 24B of the carrier car 14 and at the other end to what is generally the upper rotary plate 68A of the driven mechanism 48 via bolts 84 and nuts 86. It is contemplated, however, that the spring 66 may be connected to one of the driven mechanism 48, the drive mechanism 46, or the door 30, biasing the driven mechanism 48, the drive mechanism 46, and the door 30 to the door-closed position. For example, the spring 66 may be connected to the drive mechanism 46 and a side wall of the carrier car 14 or, in addition thereto or as an alternative thereto, the spring 66 may be connected to the door 30 and a portion of the carrier car 14. When connected to the drive mechanism 46, for example, the spring 66 may be used to bias the middle rotary arm 52 to the greater angular projection in the door-closed position so that as the middle rotary arm 52 disengages from the stabilizer 44, the spring 66 relaxes from a tensed state to project the middle rotary arm 52 to the door-closed position. Further, when the spring 66 is connected to the door 30, for example, the spring 66 may be used to bias the door 30 to the door-closed position. As such, as the middle rotary arm 52 disengages from the stabilizer 44, the drive and driven mechanisms 46, 48 are no longer forced into the door-open position and the spring 66 relaxes to pull the door 30 closed and, thereby, move the drive and driven mechanisms 46, 48 to the respective door-closed positions.

In the exemplary embodiment illustrated in FIGS. 4A, 4B, 4E, 5A, 6A, and 7A, the spring 66 is connected to the driven mechanism 48 and a side wall of the carrier car 14. Here, the spring 66 provides a force to the upper rotary plate 68A so that the spring 66 normally is biasing the doors 30 to a closed position (i.e., the spring places a force on the upper rotary plate 68A counter to the clockwise horizontal rotational movement of the upper and lower rotary plates 68A and 68B). As such, when the doors 30 of the carrier car 14 are in the door-closed position, the spring 66 is in a relaxed, non-extended, or at least not substantially extended, state. When, however, the doors 30 are in the door-open position, or are in the process of opening, as directed by movement of the middle rotary arm 52 along the stabilizer 44, the spring 66 extends or is extended with the clockwise horizontal rotational movement of the rotary plates 68. The spring 66, having an inherent tendency or desire to contract to its relaxed, non-extended state, applies a counter-directional pulling force (i.e., a force counter to the clockwise horizontal rotational movement) on the rotary plates 68 that are rotating or rotated through the door-opening process. While the counter-directional pulling force applied by the spring 66 to the rotary plates 68 is insufficient to overcome and prevent the clockwise horizontal rotational movement of the rotary plates 68, it is sufficient to initiate, or at least facilitate, the counterclockwise horizontal rotational movement of the rotary plates 68 and the door-closing process when the middle rotary arm 52 is no longer depressed into its substantially vertical orientation by the stabilizer 44. The spring 66 may be a tension spring or any other device capable of adequately performing the functions of the spring 66 described herein.

The pivot bar 72, shown most clearly in FIG. 9, generally comprises a circular base and a cylindrical post extending substantially vertically therefrom. The circular base generally includes one or more apertures through which one or more of any variety of connectors, such as bolts, screws, or nails, may pass to fixedly secure the pivot bar 72 to the exterior top wall 24B of the carrier car 14. The cylindrical post of the pivot bar passes through an aperture in each of the lower rotary plate 68B, a bearing 88 (or washer or other rotational movement facilitating devices) the rotary arm 76, another bearing 88, and the upper rotary plate 68A. Thereby, the upper and lower rotary plates 68A, 68B and the rotary arm 76 are rotatably connected about the cylindrical post of the pivot bar such that the rotary plates 68A, 68B and the rotary arm 76 may rotate horizontally, both clockwise and counterclockwise, in synchronization. The rotary plates 68, rotary arm 76, and bearings 88 are secured in their rotatable connection with the pivot bar 72 by a pivot bar plate 74 placed on top of the upper rotary plate 68A and fitted into a groove near a top end of the cylindrical post and a nut 86, or other securing device, secured over the pivot bar plate 74 to the top of the cylindrical post.

The rotary plates 68 generally comprise a connecting portion and a magnet support portion. The connecting portion comprises the aperture described above through which the cylindrical post of the pivot bar 72 passes and a plurality of additional apertures for passages of bolts 84 for the securing of rotary arm stops 90A, 90B between the upper and lower rotary plates 68A, 68B. In one exemplary embodiment, shown in FIGS. 9A and 9B, the magnet support portion branches out from the connecting portion such that the rotary plates generally assumes a U-like shape. In this embodiment, the magnets 70 are supported at or near the end of the magnet support portion distal from the connecting portion. In another exemplary embodiment, shown in FIG. 9C, the magnet rotary plates 68 assume a substantially triangular shape into which the connecting and magnet support portions are integrated.

Figure 9A:
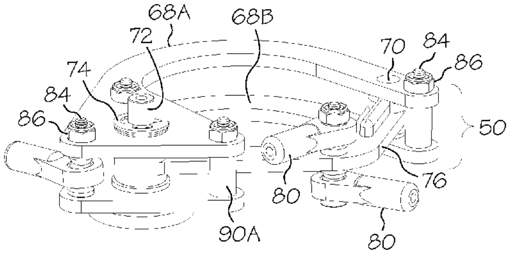
FIGS. 9A and 9B are illustrations of an isolated view and an exploded view of a driven mechanism according to another embodiment of the present invention.
Figure 9B:
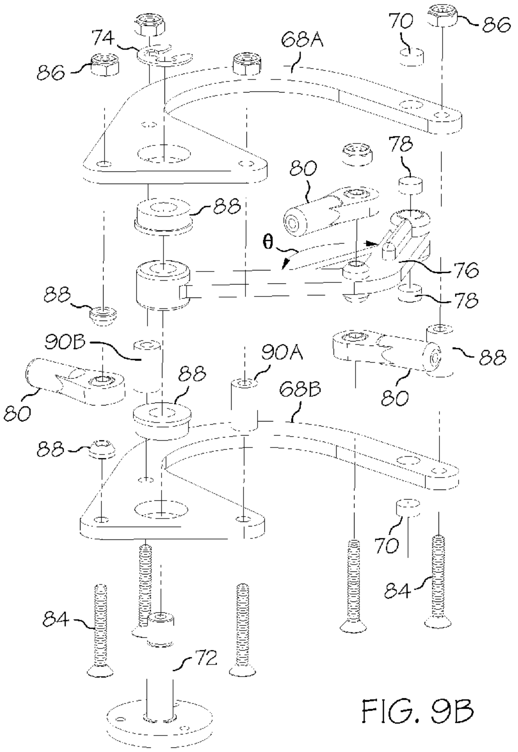
Figure 9C:
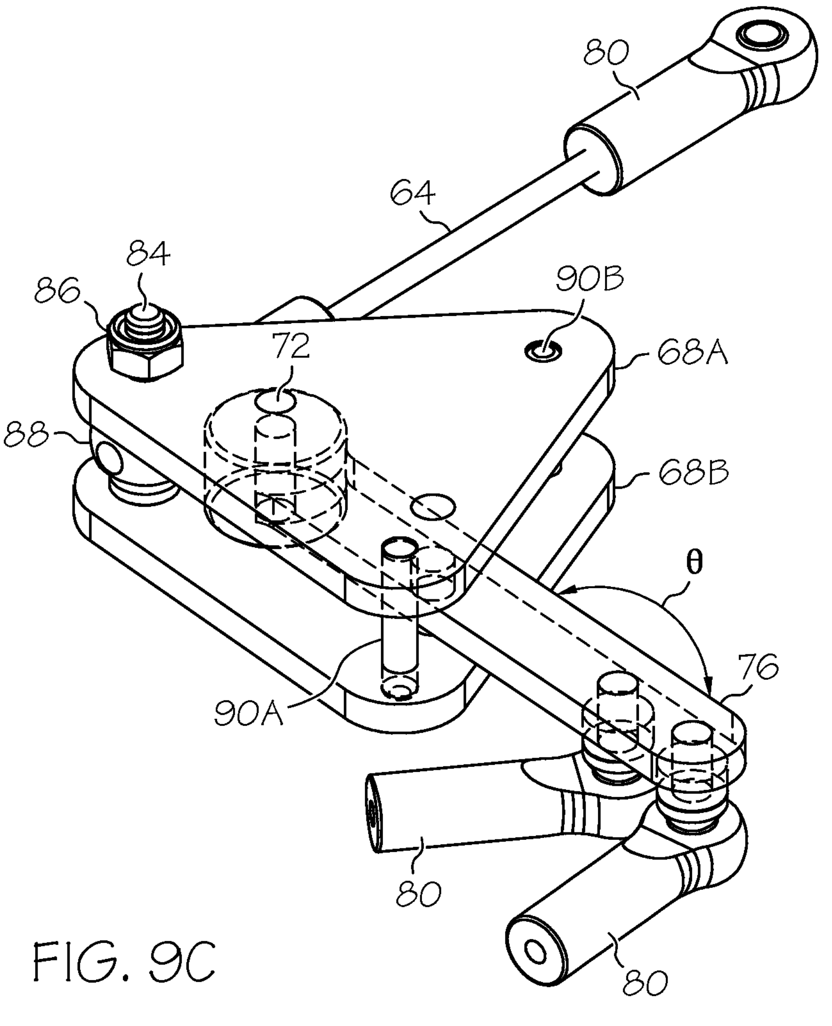
FIG. 9C is an illustration of an isolated view of a driven mechanism according to another embodiment of the present invention.

In the exemplary embodiment shown in FIGS. 9A and 9B, the rotary arm 76 comprises an angular shape generally having an angle θ of between about 90 degrees and about 120 degrees. In the exemplary embodiment shown in FIG. 9C, however, the rotary arm 76 comprises a linear shape, wherein it has an angle θ of about 180 degrees. It is contemplated, however, that an angular shape of the rotary arm 76 may have an angle θ of any between about 0 degrees and about 180 degrees as long as the rotary arm 76 may adequately perform the functions described herein.

Generally, two rods 82 are coupled via two ball joints 80 or other pivotal securing methods to the rotary arm 76 with one ball joint 80 and rod 82 coupled to a top surface of the rotary arm 76 and a second ball joint 80 and rod 82 coupled to a bottom surface of the rotary arm 76, as shown in FIG. 9. Another end of the rods 82 opposite the end connected to the rotary arm 76 is rotatably coupled to the doors 30 via additional ball joints 80, or other pivotable securing mechanisms. As such, with rotational movement of the middle rotary arm 52, the end rotary arm 58, and the driven mechanism 48 (i.e., the connected upper and lower rotary plates 68A and 68B and the rotary arm 76), the rods 82 push the doors 30 to an open position or pull the doors 30 to a closed position. It is contemplated that the rods 82 may have one of any variety of cross-sectional shapes and/or may be threaded and unthreaded.

The magnetic release mechanism 50 is generally defined by the rotary plate magnet 70 and the rotary arm magnet 78, as set forth above in the exemplary embodiment. The rotary arm 76 rotates, both clockwise and counterclockwise, in synchronization with the rotary plates 68 via the magnetic release mechanism 50 in the magnetically coupled state. In other words, the rotary plate magnets 70 magnetically couple to the rotary arm magnet 78, thus holding the rotary arm 76 in rotational synchronization, both clockwise and counterclockwise, with the rotary plates 68. Thereby, the magnetic release mechanism synchronously moves with the driven mechanism 48, and the drive mechanism 46, between a door-closed position and a door-open position when in a magnetically coupled state. When a user applies a manual force in an effort to manually close or open the doors and that force exceeds the magnetic force holding the rotary arm magnet 78 to the rotary plate magnets 70, the magnetic release mechanism 50 releases to a magnetically de-coupled state so that the rotary arm 76 may rotate independently of and relative to the rotary plates 68, thus permitting the doors 30 to close or open manually.

It is contemplated that any number of magnets 70, 78 may be provided so long as the magnetic release mechanism 50 adequately performs as described herein. Further, while repeated reference is made herein to the magnets 70, 78 of the magnetic release mechanism 50, it is contemplated that spring plungers, or other devices that may perform the functions of the magnets 70, 78 as described herein may be utilized in addition to or as an alternative to the magnets 70, 78. Due to the pressures involved, the spring pins generally operate against metal. Further, while exemplary shapes, angles, dimensions, configurations, etc., of the various systems and components of the present invention are provided herein, it is contemplated that alternatives to the foregoing may be provided and/or utilized as long as embodiments of the carrier car door assembly 12 adequately function as described herein.

Door-Opening Process: As the carrier car 14 is being transported between stations by the track system 16 of the carrier car door assembly 12, the middle rotary arm 52 projects at an angle α relative to the exterior back wall 24A of the carrier car 14. The door-opening process begins when the angularly projecting middle rotary arm 52 engages a stabilizer 44 at a station. Upon arrival at a station, the wheel 62 at the distal end of the angularly projecting middle rotary arm 52 engages the ramped portion 44A of the stabilizer 44. As the wheel 62 rolls along and advances up the ramped portion 44A, the increasing slope of the ramped portion 44A forces the middle rotary arm 52 to rotate about its rotatable joint 53 such that the middle rotary arm 52 rotates vertically upward about a horizontal axis to a position substantially parallel to the back wall 24A. As such, with the upward rotational movement of the middle rotary arm 52 toward the exterior back wall 24A, the angle α of projection of the middle rotary arm 52 relative to the exterior back wall 24A collapses to about 10 degrees, or more particularly, to about 0 degrees.

The upward rotational movement of the middle rotary arm 52 toward the back wall 24A actuates the angular joint 56, which in turn, translates the upward rotational movement of the middle rotary arm 52 into clockwise horizontal rotational movement of the end rotary arm 58. The clockwise horizontal rotational movement of the end rotary arm 58 actuates the extension rod 64 such that the extension rod 64 is pulled toward the exterior back wall 24A. This pulling of the extension rod 64 rotates the driven mechanism 48 in the clockwise horizontal direction (the synchronized clockwise horizontal rotational movement of the rotary plates 68 and the rotary arm 76 magnetically coupled to the rotary plates 68 via the magnetic release mechanism 50 about the pivot bar 72), causing the doors 30 to automatically open. It should be noted that, due to the interconnected relationship between these components of the drive mechanism 46, the rotation of the middle rotary arm 52, the rotation of the end rotary arm 58, and the actuation of the extension rod 64 occur substantially simultaneously.

Figure 11:
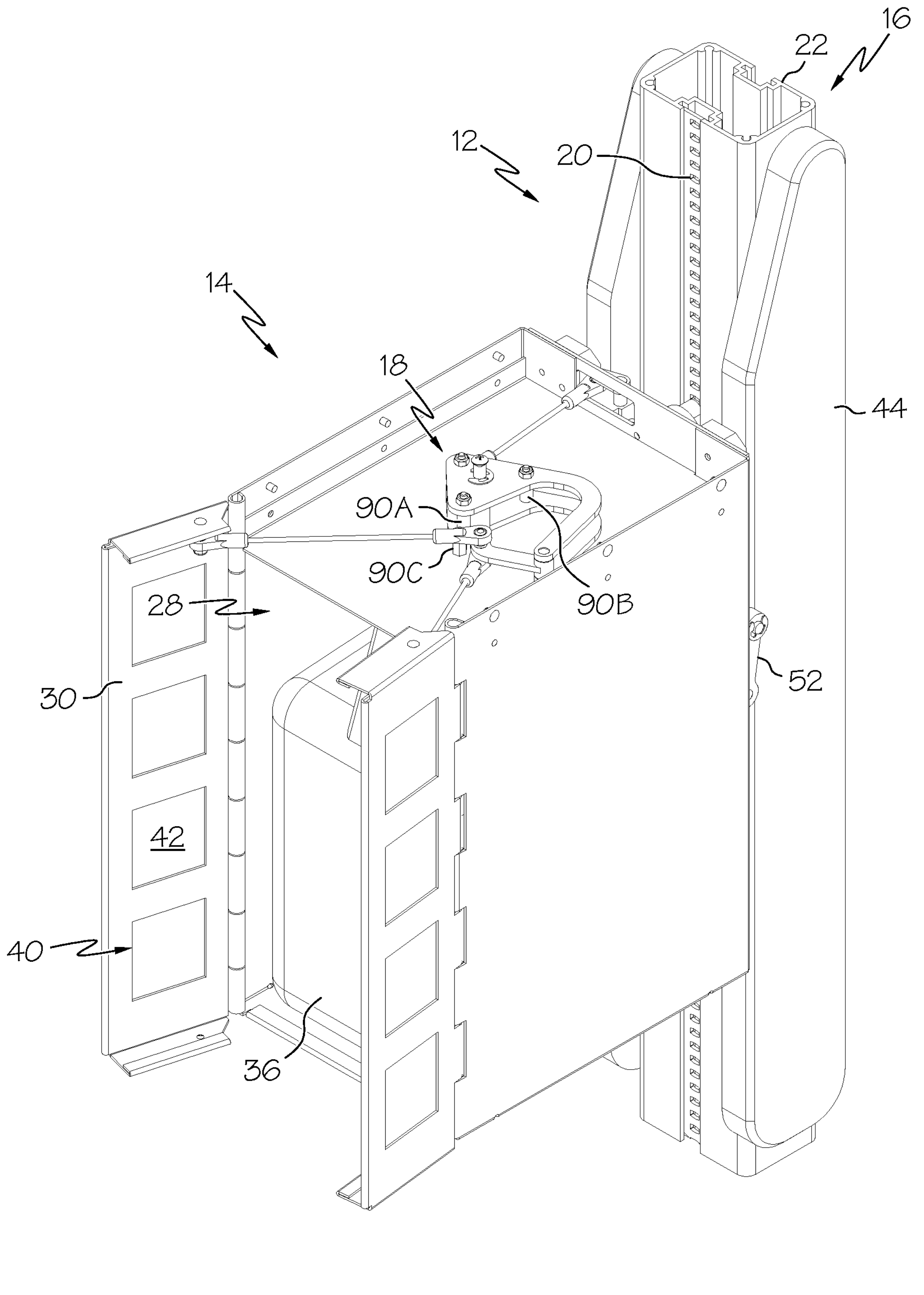
FIG. 11 is an illustration of a perspective view of a carrier car door assembly according to another embodiment of the present invention.

The clockwise rotational movement of the rotary plates 68 extends the spring 66 from its normally relaxed, non-extended, state to an extended position. In rotating clockwise, the rotary plates 68 and the rotary arm 76 push and/or actuate the rods 82 which are coupled to the rotary arm 76 forward, in so doing, advance the doors 30 to the door-open position. The driven mechanism 48 rotates clockwise until the rotary arm 76 confronts at least one of the rotary arm stops 90A, 90C that precludes further clockwise rotation of the driven mechanism 48. This progression of clockwise rotation by the driven mechanism 48 is sufficient to place the doors 30 in a fully opened, or substantially fully opened, position at either of the customer station or the teller station, as shown in FIGS. 6, 10, and 11.

Door-Closing Process: After a customer at the customer station or a representative of the facility at the teller station places one or more materials in the interior chamber 28 of the carrier car 14, the customer or representative may press a button of the carrier car door assembly 12, or otherwise activate transport of the carrier car 14 in a manner recognized and accepted by the carrier car door assembly 12, the carrier car 14 begins to transport along the track system 16 to the opposite station. With the instruction to transport the carrier car 14 to the opposite station, the wheel 62 of the middle rotary arm 52, initially positioned along, and depressed by, the level portion 44B of the stabilizer 44, moves along the level portion 44B and down the ramped portion 44A. As the wheel 62 advances down the ramped portion 44A, the spring 66, being relieved of the pressure from being forced into the extended state by the presence of the middle rotary arm 52 over the level portion 44B of the stabilizer 44, begins to contract, thereby setting into motion the counterclockwise rotation of the driven mechanism 48, which pulls the doors 30 to the door-closed position, as shown in FIGS. 5A, 5B, 7A, and 7B. The counterclockwise rotation of the driven mechanism 48 actuates the extension rod 64 by directionally pulling it away from the end rotary arm 58. This actuation of the extension rod 64 causes the end rotary arm 58 to rotate counterclockwise about its rotatable joint 59. The counterclockwise rotation of the end rotary arm 58 actuates the angular joint 56, which translates the counterclockwise rotation of the end rotary arm 58 into downward vertical rotation of the middle rotary arm 52 about its rotatable joint 53. As such, the middle rotary arm 52 rotates from a substantially vertical orientation to a substantially horizontal orientation with respect to the exterior back wall 24A and, thereby, re-assumes its angular projection relative to the exterior back wall 24A once the wheel 62 fully departs from and disengages the stabilizer 44 and the spring 66 is fully, or substantially fully, contracted. The doors 30 will remain in the door-closed position and the middle rotary arm 52 in its angular projection until the carrier car 14 arrives at the stabilizer 44 at another station, during which time the automatic door-opening and door-closing processes will repeat. The doors 30, however, may be manually opened and/or closed via a temporary release of the magnetic release 50 mechanism and move to the magnetically de-coupled state.

As mentioned above, the magnetic release mechanism 50 is generally defined by the rotary plate magnets 70 and the rotary arm magnet 78. A magnetic relationship exists between the rotary plate magnets 70 and the rotary arm magnet 78, which are oppositely charged so as to maintain the magnetic attraction there-between and the magnetic release mechanism 50 in the magnetically coupled state. The magnetic attraction between the magnets 70 and 78 possesses a strength sufficient to maintain the magnetic relationship there-between and, thus, the magnetically coupled state of the magnetic release mechanism 50, throughout clockwise and counterclockwise horizontal rotation of the driven mechanism 48 with the automatic opening and closing of the doors 30 of the carrier car 14, yet insufficient to prevent decoupling of the magnetic relationship and the release of the magnetic release mechanism 50 to the magnetically de-coupled state such that the rotary arm 76 may laterally rotate independently of the rotary plates 68 when a force in excess of a predetermined amount is applied to the doors 30 of the carrier car 14, such as when a user applies a manual force to the doors 30 to the door-open or door-closed positions. Further, the magnetic attraction is sufficient such that the magnetic relationship between the magnets 70 and 78 may repeatedly de-couple and re-couple without compromising the integrity of the magnetic release mechanism 50 and/or the linkage system 18. Therefore, as shown in FIG. 4, a user of the carrier car door assembly 12 may open or close the doors 30 manually by applying a force sufficient to overcome the magnetic attraction between the magnets 70 and 78 and, thereby, de-couple the magnetic relationship there-between and release the magnetic release mechanism 50 to the magnetically de-coupled state to permit the rotary arm 76, and the rods 82 coupled thereto, to rotate independently of the rotary plates 68 and the drive mechanism 46, which are prevented from rotating to, and remain in, the door-open position due to the position of the carrier car 14 adjacent to the stabilizer 44. The rotary arm 76 may rotate independently counterclockwise until it confronts a second rotary arm stop 90B. It is also contemplated that a user may accelerate the opening and/or closing of the doors 30 manually during the automatic door-opening and door-closing processes.

Once the doors 30 are manually opened or closed, the rotary plates 68, and the magnets thereof 70, will realign with the rotary arm 76, and the magnet thereof 78, during the immediately subsequent automatic door-opening or door-closing process with the rotation of the drive and driven mechanisms 46, 48. With this realignment, the magnetic attraction between the magnets 70 and 78 re-establishes the magnetic relationship there-between and magnetically couple in what generally is the door-closed position. As such, the magnetic release mechanism 50 moves to the magnetically coupled state. More particularly, for example, after a user has manually closed the doors 30 and the carrier car 14 leaves the stabilizers 44, the door-closing process for both the drive and driven mechanisms 46, 48 begins with the contraction of the spring 66 toward its relaxed, non-extended state, as described above. As this happens, the rotary plates 68, and the magnets 70 thereof, rotate counterclockwise, thereby realigning the magnets 70 with the magnets 78 of the rotary arm 76 and re-coupling the magnetic release mechanism 50 in the magnetically coupled state.

The magnetic release mechanism 50 ensures that minimal load pressure is applied to the drive and driven mechanisms 46, 48 from the user's applied force in manually opening and/or closing the doors 30. Further, the rotary arm 76 has the rotational freedom about the pivot bar 72 to allow the doors 30 to open (to the extent permitted by the rotary arm stop 90A) and/or close completely after the magnets 70, 78 have de-coupled. This ensures a positive open and close feature of the doors 30, meaning that the doors 30 will remain open or closed and not inadvertently re-open until activation of the immediately subsequent door-opening or door-closing process. Thereby, users do not repeatedly attempt to manually open or close a door 34 that won't stay open or closed as desired.

While certain representative details have been shown for purposes of illustrating an embodiment of the invention, it will be apparent to those persons skilled in the art that various changes in the methods and apparatus disclosed herein may be made without departing from the scope of the invention. Further, the embodiments described and illustrated herein are provided for exemplary purposes only and various other embodiments may be derived therefrom.

For the purposes of describing and defining the exemplary embodiments, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue. It is further noted that terms like "generally," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in any particular embodiment of the present invention. Further, having described exemplary embodiments of the present invention in detail, it will be apparent that modifications and variations are possible without departing from the scope of the embodiments defined in the appended claims.

What is claimed is:

1. A carrier car door assembly, comprising:

a drive mechanism movable between a door-closed position and a door-open position;

a door for a carrier car movable between a door-closed position and a door-open position;

a driven mechanism connected between the drive mechanism and the door and movable between a door-closed position and a door-open position, the driven mechanism comprising:

a linkage having a first end and a second end, the second end of the linkage including a first magnet;

an arm pivotably connected to the first end of the linkage, the arm comprising a second magnet at an end opposite its pivotal connection with the linkage, wherein:

when the driven mechanism is in a magnetic coupled state, the arm is positioned relative to the linkage such that the second magnet of the arm is aligned with and magnetically coupled with the first magnet of the linkage, and when the driven mechanism is in a magnetic de-coupled state, the arm is positioned relative to the linkage such that the second magnet of the arm is misaligned with and magnetically de-coupled with the first magnet of the linkage;

wherein the door is connected to the arm such that when the driven mechanism is in the magnetic coupled state, the drive mechanism drives the driven mechanism between the door-open and door-closed positions;

wherein when the driven mechanism is in the magnetic de-coupled state, the drive mechanism cannot drive the driven mechanism between the door-open and door-closed positions.

2. The carrier car door assembly according to claim 1, wherein the drive mechanism engages a stabilizer positioned at station of carrier car track system and moves from the door-closed position to the door-open position.

3. The carrier car door assembly according to claim 1, wherein the drive mechanism further comprises a middle rotary arm, an end rotary arm, an angular joint, and an extension rod that synchronously move between the door-closed position and the door-open position.

4. The carrier car door assembly according to claim 3, wherein the extension rod is coupled to the driven mechanism.

5. The carrier car door assembly according to claim 1, wherein the driven mechanism comprises a pivot bar, a rotary plate rotatably coupled to the pivot bar, a rotary arm rotatably coupled to the pivot bar, and a rod rotatably coupled at one end to the rotary arm and at another end to the door of the carrier car.

6. The carrier car door assembly according to claim 5, wherein the magnetic release mechanism is defined by a rotary plate magnet and a rotary arm magnet that magnetically couple and magnetically de-couple with movement of the magnetic release mechanism between the magnetically coupled state and the magnetically de-coupled state, respectively.

7. The carrier car door assembly according to claim 6, wherein the rotary arm, the rotary arm magnet, and the rod move to the door-closed position while the rotary plate, the rotary plate magnet, and the drive mechanism remain in the door-open position with the release of the magnetic release mechanism to the magnetically de-coupled state.

8. The carrier car door assembly according to claim 1, further comprising a spring connected to one of the driven mechanism, the drive mechanism, or the door, biasing the driven mechanism, the drive mechanism, and the door to the door-closed position.

9. The carrier car door assembly according to claim 8, wherein the spring is connected to the driven mechanism and a side wall of the carrier car.

10. The carrier car door assembly according to claim 8, wherein the spring is connected to the drive mechanism and a side wall of the carrier car.

11. The carrier car door assembly according to claim 8, wherein the spring is connected to the door and a portion of the carrier car.

12. The carrier car door assembly according to claim 1, wherein the drive mechanism moves the driven mechanism and the door from the door-closed position to the door-open position as the carrier car arrives at a teller or customer station.

13. A carrier car door assembly, comprising:

a track system comprising two or more stations;

a carrier car connected to the track system such that the carrier car travels along the track system between the two or more stations, the carrier car comprising a body and a door connected to the body and movable between a door-closed position and a door-open position; and a linkage system connected to the carrier car and comprising:

a drive mechanism movable between a door-closed position and a door-open position, and a driven mechanism connected between the drive mechanism and the door and movable between a door-closed position and door-open position, the driven mechanism comprising:

a plate having a first end and a second end, the second end of the plate including a first magnet;

an arm pivotably connected to the first end of the plate, the arm comprising a second magnet at an end opposite its pivotal connection with the plate, wherein:

when the driven mechanism is in a magnetic coupled state, the arm is positioned relative to the plate such that the second magnet of the arm is aligned with and magnetically coupled with the first magnet of the plate, when the driven mechanism is in a magnetic de-coupled state, the arm is positioned relative to the plate such that the second magnet of the arm is misaligned with and magnetically de-coupled with the first magnet of the plate;

wherein the door is connected to the arm such that when the driven mechanism is in the magnetic coupled state, the drive mechanism drives the driven mechanism between the door-open and door-closed positions;

wherein when the driven mechanism is in the magnetic de-coupled state, the drive mechanism cannot drive the driven mechanism between the door-open and door-closed positions.

14. The carrier car door assembly according to claim 13, further comprising a spring connected to one of the driven mechanism, the drive mechanism, or the door, biasing the driven mechanism, the drive mechanism, and the door to the door-closed position.

15. The carrier car door assembly according to claim 13, wherein the driven mechanism comprises a pivot bar, a rotary plate rotatably coupled to the pivot bar, a rotary arm rotatably coupled to the pivot bar, and a rod rotatably coupled at one end to the rotary arm and at another end to the door of the carrier car.

16. The carrier car door assembly according to claim 15, wherein the magnetic release mechanism is defined by a rotary plate magnet and a rotary arm magnet that magnetically couple and magnetically de-couple with movement of the magnetic release mechanism between the magnetically coupled state and the magnetically de-coupled state, respectively.

17. The carrier car door assembly according to claim 13, wherein the drive mechanism engages the stabilizer as the carrier car arrives at one of the two or more stations and moves the drive mechanism from the door-closed position to the door-open position.

18. The carrier car door assembly according to claim 13, wherein the drive mechanism comprises a middle rotary arm that engages the stabilizer such that the middle rotary arm rotates to the door-open position when the carrier car arrives at any of the two more stations and disengages the stabilizer such that the middle rotary arm rotates to the door-closed position when the carrier car departs from any of the two or more stations.

19. A carrier car door assembly, comprising:

a track system comprising two or more stations;

a carrier car connected to the track system such that the carrier car travels along the track system between the two or more stations, the carrier car comprising a body and a door connected to the body and movable between a door-closed position and a door-open position; and a linkage system connected to the carrier car and comprising:

a drive mechanism movable between a door-closed position and a door-open position, and a driven mechanism connected between the drive mechanism and the door and movable between a door-closed position and door-open position, the driven mechanism comprising:

a plate having a first end and a second end, the second end of the plate including a first magnet;

an arm pivotably connected to the first end of the plate, the arm comprising a second magnet at an end opposite its pivotal connection with the plate, wherein:

when the driven mechanism is in a magnetic coupled state, the arm is positioned relative to the plate such that the second magnet of the arm is aligned with and magnetically coupled with the first magnet of the plate, when the driven mechanism is in a magnetic de-coupled state, the arm is positioned relative to the plate such that the second magnet of the arm is misaligned with and magnetically de-coupled with the first magnet of the plate;

a spring connected between the body of the carrier car and the plate and biasing the door to a normally closed position;

wherein the door is connected to the arm such that when the driven mechanism is in the magnetic coupled state, the drive mechanism drives the driven mechanism between the door-open and door-closed positions;

wherein when the driven mechanism is in the magnetic de-coupled state, the drive mechanism cannot drive the driven mechanism between the door-open and door-closed positions.

* * * * *